United States Patent [19]

Beschke et al.

[11] 4,171,444

[45] Oct. 16, 1979

[54] PROCESS FOR THE PRODUCTION OF SUBSTITUTED PYRIDINE (C)

[75] Inventors: Helmut Beschke; Heinz Friedrich; Axel Kleeman, all of Hanau, Fed. Rep. of Germany

[73] Assignee: Deutsche Gold- und Silber-Scheideanstalt vormals Roessler, Frankfurt, Fed. Rep. of Germany

[21] Appl. No.: 830,985

[22] Filed: Sep. 6, 1977

[30] Foreign Application Priority Data

Aug. 16, 1977 [DE] Fed. Rep. of Germany ....... 2736791

[51] Int. Cl.² .......................................... C07D 213/08
[52] U.S. Cl. ..................................... 546/250; 544/37; 544/238; 544/360; 546/159; 546/251
[58] Field of Search ................... 260/290 P; 546/159, 546/250, 251; 544/238, 360

[56] References Cited

U.S. PATENT DOCUMENTS

| | | | |
|---|---|---|---|
| 2,877,228 | 3/1959 | Mahan | 260/290 P |
| 3,898,177 | 8/1975 | Beschke et al. | 260/290 R X |
| 3,917,542 | 11/1975 | Beschke et al. | 260/290 P X |
| 3,932,421 | 1/1976 | Minato et al. | 260/290 P |
| 3,960,766 | 6/1976 | Beschke et al. | 260/290 R X |

OTHER PUBLICATIONS

Vereshchagin et al., Russian Chemical Reviews, vol. 30, pp. 426 to 429 (1961).
Krohnke, Synthesis, pp. 1–24 (1976).

Primary Examiner—John D. Randolph
Attorney, Agent, or Firm—Cushman, Darby & Cushman

[57] ABSTRACT

Pyridines substituted in the 2- and 6-positions by an aromatic or heteroaromatic group are prepared by reacting an aromatic or heteroaromatic ketone having at least one reactive methylene group adjacent to the keto group with an aliphatic aldehyde and ammonia in the presence of a dehydrating and dehydrogenating catalyst at a temperature of about 250° to 550° C.

23 Claims, No Drawings

PROCESS FOR THE PRODUCTION OF SUBSTITUTED PYRIDINE (C)

BACKGROUND OF THE INVENTION

The invention is directed to a process for the production of pyridines substituted in the 2- and 6-positions by an aromatic or heteroaromatic group. These substituted pyridines are important intermediate products for the production of medicines, plant protective agents and synthetic resins.

It is known that 2,6-diphenyl pyridine is formed when diphenyl pyridone dicarboxylic acid ester is distilled in the presence of zinc dust. The ester is recovered by dehydrogenation of the diphenyl piperidone dicarboxylic acid ester formed in the reaction of acetone dicarboxylic acid ester with benzaldehyde and ammonia (Berichte Vol. 42 (1910) pages 2020–2025). It is also known to start from acetophenone in production of the 2,6-diphenyl pyridine. For this purpose acetophenone is condensed with phenyl propargyl aldehyde to 1,5-diphenylpentin-(1)-en-(3)-one-(5), this reacted with perchloric acid to form 2,6-diphenyl pyrylium perchlorate and this finally converted by means of ammonia into the 2,6-diphenyl pyridine (Berichte Vol. 93 (1960) pages 1253–1256). There is also obtained 2,6-diphenyl pyridine from acetophenone and N,N,N-trimethylhydrazonium tetrafluoroborate or in a corresponding manner from 4-methyl acetophenone there is formed 2,6-diphenyl-3,5-dimethyl pyridine or from propiophenone there is formed 2,6-di-p-tolyl pyridine (J. Amer. Chem. Soc. Vol. 88 (1966) pages 3654–3655). It is further known to recover 2,6-diphenyl pyridine and various substituted 2,6-diphenyl pyridine by dehydrogenation of the corresponding piperidines by means of sulfur. The piperidines are produced by reduction of the corresponding 4-piperidone (J. Indian Chem. Soc. Vol. 32 (1955) pages 274–278).

Besides it is known that 2,6-bis(2'-pyridyl)-pyridine can be recovered by decarboxylation of 2,6-bis (2'-pyridyl)-pyridine-3,5-dicarboxylic acid. The carboxylic acid is accessible in several steps from 2,6-bis(2'-pyridyl)-3,5-di-carbethoxy-1,4-dihydropyridine resulting from the reaction of ethyl picolinoyl acetate with formaldehyde (J. Org. Chem. Vol. 26 (1961) pages 4415–4418).

Furthermore, it is known that 2,6-bis(2'-pyridyl)-pyridine is formed as a byproduct besides 2-(2'-pyridyl)-pyridine in the reaction of pyridine with potassium peroxydisulfate (East German Patent No. 23,118) or with pyridine-N-oxide in the presence of Pd-Pt-catalysts (Yakugaku Zasshi Vol. 93 (1973) pages 144–148). Also in the heating of pyridine in the presence of Raney nickel there is formed as byproduct 2,6-bis(2'-pyridyl)-pyridine and in the same manner there is formed in the heating of substituted pyridines the corresponding substituted compounds (J. Chem. Soc. (1956) pages 616–620). 2,6-Bis(3-pyridyl)-pyridine is produced when 3-acetyl pyridine is reacted with dimethylamine hydrochloride and formaldehyde to form an aminoketone and this aminoketone is further reacted with 3-pyridinium acetyl pyridine bromide obtained from 3-acetyl pyridine by way of 3-bromoacetyl pyridine (Synthesis (1976) pages 1–24).

Finally, it is known to produce 2,6-bis(2'-thienyl)-pyridine by reaction of 2,6-dichloropyridine with 2-lithiothiophene (Angew. Chem. Vol. 83 (1971) pages 796–799).

The known processes are little suited for use on an industrial scale. They are expensive and cumbersome to handle or give the desired compounds only in low yield or as byproducts. Besides in several cases the necessary starting materials are only accessible with difficulty.

SUMMARY OF THE INVENTION

There has now been found a process for the production of pyridines substituted in the 2- and 6-positions with an aromatic or heteroaromatic group by the catalytic reaction of an aromatic ketone or heteroaromatic ketone having at least one reactive methylene group adjacent to the keto group with a saturated aliphatic aldehyde in the gas phase and with ammonia and in the presence of a dehydrating and dehydrogenating catalyst at a temperature of about 250° to 550° C. In this process a pyridine substituted in the 2- and 6-positions by an aromatic or heteroaromatic group is produced from simple, easily accessible substances in a single step reaction. High yields are produced. The process in contrast to the known processes is distinguished by being suited for use on an industrial scale.

According to the invention (1) an aromatic or heteroaromatic substituted ketone of the general formula

in which $R_1$ is an aromatic or heteroaromatic ring which in a given case is substituted with one or more halogens, alkyl or cyano groups, $R_2$ is hydrogen or a lower alkyl group which can be branched or straight chain, the alkyl group preferably has 1 to 6, particularly 1 to 2 carbon atoms, is reacted (2) with an aldehyde of the formula

in which $R_3$ is hydrogen or a branched or straight chain alkyl group preferably with 1 to 6, particularly 1 to 2 carbon atoms and (3) ammonia to form a compound of the general formula

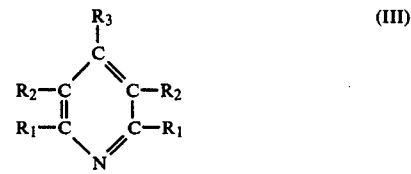

in which $R_1$, $R_2$ and $R_3$ are as defined above.

As aromatic or heteroaromatic ketones (I) there can be used for example 4-methyl acetophenone, 3-methyl acetophenone, 4-ethyl acetophenone, 2,4-dimethyl acetophenone, 4-butyl acetophenone, 4-sec.butyl acetophenone, 4-chloro acetophenone, 2,4-dichloro acetophenone, 4-bromo acetophenone, 4-fluoro acetophenone, 2-methyl-4-chloro acetophenone, 2-acetyl pyrane, caprophenone, laurophenone, myristophenone, 4-cyano acetophenone, acetyl azulene, acetyl phenthiazine, acetyl triazole, acetyl anthracene, 2-acetyl naphthalene, 2-methyl-3-acetyl thiophene, 5-methyl-3-acetyl furane, preferably 3-acetyl thiophene, 2-acetyl naphthalene, 3-acetyl furane, 2-acetyl quinoline, acetyl quinolines with the acetyl group in the 3-, 4-, 5-, 6- or 7-position, acetyl thiazole, e.g., 2-acetyl thiazole and 4-acetyl thiazole, acetyl toluene, e.g., 4-methyl acetophenone and 3-methyl acetophenone, acetyl indole, e.g., 2-acetyl indole, acetyl indene, e.g., 1-acetyl indene and 2-acetyl indene, acetyl N-methyl pyrrole, e.g., 3-acetyl N-methyl pyrrole and 2-acetyl N-methyl pyrrole, acetyl pyrimidine, e.g., 4-acetyl pyrimidine, acetyl thiopyrane, e.g., 2-acetyl thiopyrane, acetyl oxazole, e.g., 2-acetyl oxazole, acetyl pyrazine, e.g., 2-acetyl pyrazine, n-butyrophenone, n-valerophenone, isobutyrophenone and particularly acetophenone, propiophenone, 4-methyl acetophenone, 3-acetyl pyridine, 4-acetyl pyridine, 2-acetyl naphthalene and 2-acetyl thiophene.

As suitable aldehydes (II) there can be used for example unsubstituted aldehydes such as propionaldehyde, butyraldehyde, isobutyraldehyde, valeraldehyde, isovaleraldehyde, 2-methyl butyraldehyde, caproaldehyde, heptaldehyde and especially acetaldehyde and formaldehyde.

The starting materials are optionally used as solutions, for example as solutions in water or lower alkanols such as methanol, ethanol and propanol-2. The ketones and aldehydes can also be added in the form of materials which set them free under the conditions of the process, for example as hemiacetals, the aldehydes also can be added as polymerizates, the formaldehyde for example as polyformaldehyde or trioxane.

The reaction conditions such as temperature and pressure and the proportions of the reacting substances and the residence time in a given case to a certain extent are dependent upon each other according to the type of reacting substances and the type of catalyst.

In general, the reaction is carried out at a temperature between 250° and 550° C. In most cases there are preferred temperatures between 300° and 500° C., especially between 350° and 450° C. It is advantageous to work at pressures of about 1 to 4 bar. However, there can also be used lower or higher pressures although it is suitable not to substantially deviate from this pressure range since it permits the use of simple apparatus.

The proportions of ketone (I) to aldehyde (II) can be selected substantially at random, both stoichiometric as well as under or over stoichiometric being usable. Generally, it is advantageous to add about 0.2 to 2.0 moles of aldehyde (II) per mole of ketone (I). Preferably there are used about 0.3 to 1.0 moles, especially 0.4 to 0.8 moles of aldehyde (II) per mole of ketone (I).

The ammonia can be present in the reaction in substantially any proportions from under stoichiometric to over stoichiometric. In most cases it is suitable to have present at least 0.5 mole of ammonia per mole of ketone (I), however, there can be as much as about 100 moles of ammonia per mole of ketone (I). Advantageously, there are employed about 1 to 20 moles of ammonia, preferably 2 to 15 moles of ammonia, especially 3 to 12 moles of ammonia, per mole of ketone (I).

The reaction takes place in the gas phase. In a given case starting materials present in another state are first converted to the gaseous state. It can be expedient to dilute the gases of ketone (I), aldehyde (II) and ammonia with inert gases. As inert gases there can be employed, for example, steam, air and especially nitrogen. If the starting materials are used in the form of solution the gases are diluted by the solvent. Generally, it is expedient to use in all not more than about 20 moles of inert gas per mole of ketone (I). Preferably, there are used about 0.5 to 10 moles, particularly 1 to 5 mole of inert gas per mole of ketone (I).

As catalysts there can be employed those which have a dehydrating and dehydrogenating action. For example, these include the catalysts described in Hydrocarbon Processing, Vol. 47 (1968) pages 103 to 107 which are aluminum compounds such as aluminum oxide and aluminum silicate, optionally with addition of other metal oxides and fluorides. The entire disclosure of the Hydrocarbon Processing article is hereby incorporated by reference and relied upon.

With advantage there is used in the process catalysts produced according to German Offenlegungsschrift No. 2 151 417 and related Beschke U.S. Pat. No. 3,898,177; according to German OS No. 2 224 160 and related Beschke U.S. Pat. No. 3,960,766; and according to German OS No. 2 239 801 and related Beschke U.S. Pat. No. 3,917,542. The entire disclosure of Beschke U.S. Pat. Nos. 3,898,177; 3,917,542 and 3,960,766 are hereby incorporated by reference and relied upon.

These catalysts are prepared by treating with oxygen at temperatures of 550° to 1200° C. compounds of the elements Al, F and O which compounds also contain at least one element of the second, third or fourth groups of the periodic system (German Offenlegungsschrift 2 151 417 and related Beschke U.S. Pat. No. 3,898,177) or at least two elements of the second, fourth, fifth or sixth groups of the periodic system (German Offenlegungsschrift 2 224 160 and related Beschke U.S. Pat. No. 3,960,766) or at least one element of the second main group of the periodic system (German Offenelegungsschrift No. 2 239 801 and related Beschke U.S. Pat. No. 3,971,542). The catalysts are used in a fixed bed or preferably in a fluidized bed.

Beschke U.S. Pat. No. 3,898,177 describes the catalyst in claim 1 as consisting essentially of oxygen containing compounds of Al, F, at least one of the elements B and Si and at least one element from the second and fourth groups of the periodic system selected from the group consisting of Mg, Ba, Zn, Sn and Zr, said catalyst having been prepared by heating in the presence of oxygen at a temperature of 600° to 800° C:

1. aluminum, aluminum oxide or an aluminum compound convertible to the oxide at said temperature;
2. a compound of fluorine, said fluorine having been added as ammonium fluoride, ammonium hydrogen fluoride, hydrogen fluoride, fluoboric acid, fluosilicic acid, boron trifluoride, magnesium fluoborate, magnesium fluosilicate, zinc fluosilicate or barium fluosilicate;
3. boron, silicon, boric oxide, silica or a compound of boron or silica convertible to the oxide at said temperature; and,
4. magnesium, zinc, tin, zirconium, magnesium oxide, zinc oxide, tin oxide or a compound of zirconium or barium convertible to the oxide at said temperature, the atomic ratio of Al to F being from 1000:25 to 1000:800 and the atomic ratio of Al to the total of (3) and (4) being from 1000:5 to 1000:200, the atomic ratio of the total of boron and silicon to the other element from the second and fourth groups being between 1 to 10 and 10 to 1.

Beschke U.S. Pat. No. 3,917,542 in claim 1 describes the catalyst as having been prepared by heating at 600° to 800° C. In the presence of gaseous oxygen, (1) aluminum metal, aluminum oxide or a compound of aluminum convertible to the oxide upon heating with gaseous oxygen at 600° to 800° C., (2) ammonium fluoride, hydrogen fluoride or a fluoride of an element of the second main group of the periodic system and (3) at least one element of the second main group of the periodic system, the oxide of said element or a compound of said element convertible to the oxide in the presence of gaseous oxygen at a temperature of 600° to 800° C., said catalyst consisting essentially of the elements Al, F, O and the element of the second main group of the periodic system.

Beschke U.S. Pat. No. 3,960,766 in claim 1 describes the catalyst as consisting essentially of the product obtained by treating with oxygen at a temperature of 550° to 1200° C. compounds of the elements Al, F and O and at least two other elements selected from the second, fourth, fifth and sixth groups of the periodic system, said two other elements being selected from the group consisting of Mg, Ba, Zr, Sn, Ti, P, Ta, Sb and S, the ratios of the elements being Al to F of between 1000 to 10 and 1000 to 800 and of Al to the elements of the second, fourth, fifth and sixth groups being between 1000 to 5 and 1000 to 2000.

There can also be employed a procedure using the apparatus and method of German OS No. 2 449 340 and related Beschke U.S. application Ser. No. 622,488 filed Oct. 15, 1975 in which instead of the reactants mentioned in the German OS and Beschke ketone (I) and aldehyde (II) are fed into the reactor separate from the ammonia. Generally, the residence time in the reactor is between 0.2 and 5.0 seconds. The entire disclosure of the Beschke U.S. application Ser. No. 622,488 is hereby incorporated by reference and relied upon.

The working up of the gas mixture resulting from the reaction can take place in customary manner by washing the gases with a liquid, especially water or methanol and by further separation by means of extraction and distillation. With especial advantage there is employed the procedure of German OS 2 554 946 and related Beschke U.S. application Ser. No. 748,041 filed Dec. 6, 1976 in which the gas mixture is not washed but cooled and as a result partially condensed in such manner that any possible excess ammonia remains in the residual gas and with this is directly recycled.

Unless otherwise indicated all parts and percentages are by weight.

The process can comprise, consist essentially of or consist of the steps set forth and the materials can comprise, consist essentially of or consist of those set forth.

DESCRIPTION OF THE PREFERRED EMBODIMENTS

EXAMPLE 1

A fixed bed reactor with a volume of 100 ml was filled with a catalyst which was produced according to Beschke U.S. Pat. No. 3,917,542 Example 1 (and German OS No. 2 239 801) from aluminum oxide, magnesium nitrate and ammonium hydrogen fluoride in the atomic ratio aluminum to magnesium to fluorine of 1000:25:50. There was led over this catalyst hourly a gas mixture of 60 grams (0.5 mole) of acetophenone, 7.5 grams (0.08 mole) of trioxane, 44.8 normal liters (2.0 moles) of ammonia and 22.4 normal liters (1.0 mole) of nitrogen. The temperature in the reactor was held at 420° C. The acetophenone and trioxane were completely reacted.

There were recovered hourly 27.8 grams of 2,6-diphenyl pyridine. This corresponds to a yield of 48%, based on the acetophenone added. The product had a boiling point of 185° to 190° C. at 1 mbar and after recrystallization from methanol had a melting point of 82.5° C. As byproducts there were formed hourly 2.0 grams of 2,6-diphenyl-3-methyl pyridine.

In the following examples, there was used the same procedure as in Example 1.

EXAMPLE 2

| | |
|---|---|
| Starting Materials: | acetophenone, formaldehyde and ammonia in the molar ratios of 1:0.5:4 (formaldehyde added as a mixture of 30% formaldehyde and 70% water) |
| Catalyst: | As in Example 1 |
| Reaction Temperature: | 420° C. |
| Reaction: | 97% of the acetophenone |
| Product: | 2,6-diphenyl pyridine, B.P. 185° to 190° C. at 1 mbar |
| Yield: | 48% based on the acetophenone added |
| Byproduct: | 2% 2,6-diphenyl-3-methyl pyridine based on the acetophenone added |

EXAMPLE 3

| | |
|---|---|
| Starting Materials: | acetophenone, formaldehyde and ammonia in the molar ratios of 1:1:4 |
| Catalyst: | As in Example 1 |
| Reaction Temperature: | 420° C. |
| Reaction: | 85% of the acetophenone |
| Product: | 2,6-diphenyl pyridine, B.P. 185° to 190° C. at 1 mbar |
| Yield: | 34% based on the acetophenone added |
| Byproduct: | 12% 2,6-diphenyl-3-methyl pyridine based on the acetophenone added |

EXAMPLE 4

| | |
|---|---|
| Starting Materials: | acetophenone, formaldehyde and ammonia in the molar ratios of 1:0.6:4 (formaldehyde added as a mixture of 40% formaldehyde, 20% methanol and 40% water) |
| Catalyst: | As in Example 1 |
| Reaction Temperature: | 420° C. |
| Reaction: | 100% of the acetophenone |
| Product: | 2,6-diphenyl pyridine, B.P. 185° to 190° C. at 1 mbar |
| Yield: | 51% based on the acetophenone added |
| Byproduct: | 4% 2,6-diphenyl-3-methyl pyridine based on the acetophenone added |

EXAMPLE 5

| | |
|---|---|
| Starting Materials: | acetophenone, formaldehyde and ammonia in the molar ratios of 1:0.6:4 (formaldehyde added as a mixture of 40% formaldehyde, 20% methanol and 40% water) |
| Catalyst: | As in Example 1 |
| Reaction Temperature: | 330° C. |
| Reaction: | 84% of the acetophenone |
| Product: | 2,6-diphenyl pyridine, B.P. 185° to 190° C. at 1 mbar |
| Yield: | 43% based on the acetophenone added |
| Byproduct: | 11% 2,6-diphenyl-3-methyl pyridine based on the acetophenone |

EXAMPLE 6

| Starting Materials: | acetophenone, formaldehyde and ammonia in the molar ratios of 1:0.5:4 (formaldehyde added as a mixture of 60% paraformaldehyde and 40% methanol adjusted to a pH of 8 to 9) |
|---|---|
| Catalyst: | As in Example 1 |
| Reaction Temperature: | 420° C. |
| Reaction: | 100% of the acetophenone |
| Product: | 2,6-diphenyl pyridine, B.P. 185° to 190° C. at 1 mbar |
| Yield: | 50% based on the acetophenone added |
| Byproduct: | 11% 2,6-diphenyl-3-methyl pyridine based on the acetophenone added |

EXAMPLE 7

| Starting Materials: | 4-acetyl pyridine, formaldehyde and ammonia in the molar ratios of 1:0.5:4 |
|---|---|
| Catalyst: | As in Example 1 |
| Reaction Temperature: | 420° C. |
| Reaction: | 84% of the 4-acetyl pyridine |
| Product: | 2,6-bis(4'-pyridyl)-pyridine, B.P. 210° to 218° C. at 1 mbar, M.P. (after recrystallization from toluene) 143° to 144° C. |
| Yield: | 48% based on the 4-acetyl pyridine added |

EXAMPLE 8

| Starting Materials: | 3-acetyl pyridine, formaldehyde and ammonia in the molar ratios of 1:0.5:4 (formaldehyde added as a mixture of 35% formaldehyde and 65% water) |
|---|---|
| Catalyst: | As in Example 1 |
| Reaction Temperature: | 420° C. |
| Reaction: | 64% of the 3-acetyl pyridine |
| Product: | 2,6-bis(3'-pyridyl)-pyridine, B.P. 205° to 212° C. at 1 mbar, M.P. (after recrystallization from a mixture of ether and light petroleum) 81° to 83° C. |
| Yield: | 45% based on the 3-acetyl pyridine added |

EXAMPLE 9

| Starting Materials: | propiophenone, trioxane, ammonia and nitrogen in the molar ratios of 6:1:24:12 |
|---|---|
| Catalyst: | According to Beschke U.S. Pat. No. 3,960,766 Example 1a (and German OS 2 224 160) from aluminum oxide, magnesium nitrate and titanium tetrafluoride, atomic ratio aluminum to magnesium to titanium to fluorine of 1000:25:25:100 |
| Reaction Temperature: | 410° C. |
| Reaction: | 74% of the propiophenone |
| Product: | 2,6-diphenyl-3,5-dimethyl pyridine, M.P. 133° to 135° C. |
| Yield: | 49% based on the propiophenone added |

EXAMPLE 10

| Starting Materials: | p-methyl acetophenone, trioxane, ammonia and nitrogen in the molar ratios of 6:1:24:12 |
|---|---|
| Catalyst: | According to Beschke U.S. Pat. No. 3,898,177 Example 5 (and German OS 2 151 417) from aluminum oxide, magnesium nitrate and fluosilicic acid, atomic ratio aluminum to magnesium to silicon to fluorine of 1000:24:25:156 |
| Reaction Temperature: | 390° C. |
| Reaction: | 82% of the p-methyl acetophenone |
| Product: | 2,6-bis(p-methylphenyl)-pyridine, M.P. 160° to 162° C. |
| Yield: | 56% based on the p-methyl acetophenone added |

EXAMPLE 11

| Starting Materials: | 2-acetyl thiophene, formaldehyde, ammonia and nitrogen in the molar ratios of 2:1:8:4 (formaldehyde added as a mixture of 30% formaldehyde and 70% water) |
|---|---|
| Catalyst: | As in Example 1 |
| Reaction Temperature: | 420° C. |
| Reaction: | 90% of the 2-acetyl thiophene |
| Product: | 2,6-bis(2'-thienyl)-pyridine, M.P. 78° C. |
| Yield: | 50% based on the 2-acetyl thiophene added |

EXAMPLE 12

| Starting Materials: | acetophenone, acetaldehyde, ammonia and nitrogen in the molar ratios of 2:1:8:4 |
|---|---|
| Catalyst: | As in Example 1 |
| Reaction Temperature: | 400° C. |
| Reaction: | 100% of the acetophenone |
| Product: | 2,6-diphenyl-4-methyl pyridine, M.P. 74° C. |
| Yield: | 38% based on the acetophenone added |

What is claimed is:

1. A process for the production of a pyridine substituted in both the 2- and 6-positions by an aromatic or heteroaromatic group comprising catalytically reacting an aromatic or heteroacromatic group substituted ketone having at least one reactive methylene group adjacent to the keto group with a saturated aliphatic aldehyde and ammonia in the gas phase at a temperature from about 250° to 550° C. in the presence of a dehydrating and dehydrogenatating catalyst which is either (1) a catalyst consisting essentially of oxygen containing compounds of Al, F, at least one of of the elements B and Si and at least one element from the second and fourth groups of the periodic system selected from the group consisting of Mg, Ba, Zn, Sn and Zr, said catalyst having been prepared by heating in the presence of oxygen at a temperature of 600° to 800° C.;

1. aluminum, aluminum oxide or an aluminum compound convertible to the oxide at said temperature,
2. a compound of fluorine, said fluorine having been added as ammonium fluoride, ammonium hydrogen fluoride, hydrogen fluoride, fluoboric acid, fluosilicic acid, boron trifluoride, magnesium fluoborate, magnesium fluosilicate, zinc fluosilicate or barium fluosilicate,
3. boron, silicon, boric acid, silica or a compound of boron or silicon convertible to the oxide at said temperature and
4. magnesium, zinc, tin, zirconium, magnesium oxide, zinc oxide, tin oxide or a compound of zirconium or barium convertible to the oxide at said temperature, the atomic ratio of Al to F being from 1000:25 to 1000:800 and the atomic ratios of Al to the total of (3) and (4) being from 1000:5 to 1000:200, the atomic ratio of the total of boron and silicon to the other element from the second and fourth group being between 1 to 10 and 10 to 1, (2) a catalyst having been prepared by heating at 600° to 800° C. in the presence of gaseous oxygen (1) aluminum metal, aluminum oxide or a compound of aluminum convertible to the oxide upon heating with gaseous oxygen at 600° C. to 800° C., (2) ammonium fluoride, hydrogen fluoride or a fluoride of an element of the second main group of the periodic system and (3) at least one element of the second main group of the periodic system, the oxide of said element or a compound of said element convertible to the oxide in the presence of gaseous oxygen at a temperature of 600° to 800° C., said catalyst consisting essentially of the elements Al, F, O and the element of the second main group of the periodic system being selected from the group consisting of Mg, Ca, Sr and Ba, and (3) a catalyst consisting essentially of the product obtained by treating with oxygen at a temperature of 500° to 1200° C., compounds of the elements Al, F and O and at least two other elements selected from the second, fourth, fifth and sixth groups of the periodic system, said two other elements being selected from the group consisting of Mg, Ba, Zr, Sn, Ti, P, Ta, Sb, and S, the ratios of the elements being Al to F of between 1,000 to 10 and 1,000 to 800 and of Al to the elements of the second, fourth, fifth and sixth groups being between 1,000 to 5 and 1,000 to 200.

2. The process of claim 1 wherein the substituted pyridine has the formula

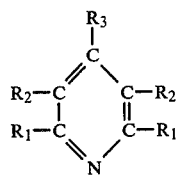
(III)

where $R_1$ is an unsubstituted aromatic or heteroaromatic ring or such a ring substituted with halogen, alkyl or cyano, $R_2$ is hydrogen or a lower alkyl group and $R_3$ is hydrogen or a lower alkyl group, the ketone has the formula $$R_1-\underset{\underset{O}{\|}}{C}-CH_2-R_2 \qquad (I)$$

and the aldehyde has the formula $$O=CH-R_3 \qquad (II)$$

3. The process of claim 2 wherein $R_2$ is hydrogen or alkyl of 1 to 6 carbon atoms and $R_3$ is hydrogen or alkyl of 1 to 6 carbon atoms.

4. The process of claim 3 wherein $R_2$ is hydrogen or alkyl of 1 to 2 carbon atoms and $R_3$ is hydrogen or alkyl of 1 to 2 carbon atoms.

5. The process of claim 2 wherein the aromatic or heteroaromatic is phenyl, thienyl, furyl, naphthyl, quinolyl, thiazolyl, pyrryl, pyrimidyl, thiopyranyl, oxazolyl, pyrazinyl or pyridyl or such a group substituted by cyano, halogen or lower alkyl.

6. The process of claim 5 wherein the ketone of formula (I) is cyanoacetophenone, chloroacetophenone, acetyl thiophene, acetyl furane, acetyl naphthalene, acetyl quinoline, acetyl thiazole, acetyl methyl pyrrole, acetyl pyrimidine, acetyl thiopyrane, acetyl oxazole, acetyl pyrazine, acetyl pyridine, methyl acetophenone or an alkyl phenyl ketone having 2 to 5 carbon atoms in the alkyl group and the aldehyde of formula (II) has 1 to 4 carbon atoms.

7. The process of claim 6 wherein the aldehyde of formula (II) is acetaldehyde or formaldehyde.

8. The process of claim 7 wherein the ketone of formula (I) is acetophenone, 4-acetyl pyridine, 3-acetyl pyridine, propiophenone, p-methyl acetophenone or 2-acetyl thiophene.

9. The process of claim 8 wherein the process is carried out at 300° to 500° C.

10. The process of claim 2 wherein the reaction temperature is 300° to 500° C.

11. The process of claim 10 wherein the reaction temperature is 350° to 450° C.

12. The process of claim 2 wherein there is used 0.2 to 2.0 moles of aldehyde (II) per mole of ketone (I).

13. The process of claim 12 wherein there is used 1 to 20 moles of ammonia per mole of ketone (I).

14. The process of claim 13 wherein the reaction is carried out in the presence of an inert gas.

15. The process of claim 8 wherein the aldehyde is formaldehyde.

16. The process of claim 7 wherein the aldehyde is formaldehyde.

17. The process of claim 5 wherein the aldehyde is formaldehyde.

18. The process of claim 2 wherein the aldehyde is formaldehyde.

19. The process of claim 1 wherein the aldehyde is formaldehyde.

20. The process of claim 19 wherein the formaldehyde is employed as formaldehyde per se, trioxane or paraformaldehyde.

21. The process of claim 10 wherein the catalyst is (1).

22. The process of claim 10 wherein the catalyst is (2).

23. The process of claim 10 wherein the catalyst is (3).

* * * * *

UNITED STATES PATENT AND TRADEMARK OFFICE
CERTIFICATE OF CORRECTION

PATENT NO. : 4,171,444
DATED : October 16, 1979
INVENTOR(S) : HELMUT BESCHKE, et al It is certified that error appears in the above—identified patent and that said Letters Patent are hereby corrected as shown below:

Claim 1, column 9, line 39, change "500°" to --550°--.

Signed and Sealed this

Twenty-second Day of January 1980

[SEAL]

Attest:

SIDNEY A. DIAMOND

Attesting Officer

Commissioner of Patents and Trademarks